(12) United States Patent
Gaska et al.

(10) Patent No.: US 7,634,996 B2
(45) Date of Patent: Dec. 22, 2009

(54) ULTRAVIOLET RADIATION STERILIZATION

(75) Inventors: Remigijus Gaska, Columbia, SC (US); Michael Shur, Latham, NY (US); Yuriy Bilenko, Columbia, SC (US)

(73) Assignee: Sensor Electronic Technology, Inc., Columbia, SC (US)

( * ) Notice: Subject to any disclaimer, the term of this patent is extended or adjusted under 35 U.S.C. 154(b) by 273 days.

(21) Appl. No.: 11/674,494

(22) Filed: Feb. 13, 2007

(65) Prior Publication Data

US 2007/0187626 A1   Aug. 16, 2007

Related U.S. Application Data

(60) Provisional application No. 60/773,131, filed on Feb. 14, 2006.

(51) Int. Cl.
*A61M 16/00* (2006.01)
(52) U.S. Cl. .................. 128/200.26; 128/207.14; 128/207.16
(58) Field of Classification Search ............. 250/455.11; 422/24; 128/200.26, 207.14, 207.16; 210/87
See application file for complete search history.

(56) References Cited

U.S. PATENT DOCUMENTS

| | | | |
|---|---|---|---|
| 3,817,703 A | | 6/1974 | Atwood |
| 5,364,645 A | | 11/1994 | Lagunas-Solar et al. |
| 6,013,918 A | * | 1/2000 | Bushnell et al. ........ 250/454.11 |
| 6,110,424 A | | 8/2000 | Maiden et al. |
| 6,248,811 B1 | * | 6/2001 | Ottersbach et al. .......... 523/423 |
| 6,443,147 B1 | * | 9/2002 | Matter .................... 128/200.26 |
| 6,565,803 B1 | | 5/2003 | Bolton et al. |
| 6,576,188 B1 | | 6/2003 | Rose et al. |
| 6,579,495 B1 | * | 6/2003 | Maiden ....................... 422/24 |
| 6,673,137 B1 | | 1/2004 | Wen |
| 6,818,177 B1 | | 11/2004 | Turcotte |
| 7,089,942 B1 | | 8/2006 | Grey |
| 7,160,370 B2 | | 1/2007 | Baca et al. |
| 2002/0074559 A1 | | 6/2002 | Dowling et al. |
| 2002/0176809 A1 | | 11/2002 | Siess |
| 2003/0194692 A1 | | 10/2003 | Purdum |
| 2005/0003323 A1 | * | 1/2005 | Katsuda et al. ............... 433/29 |
| 2006/0163126 A1 | * | 7/2006 | Maiden ....................... 210/87 |

OTHER PUBLICATIONS

International Search Report with written opinion for companion PCT Application dated Feb. 12, 2008.

* cited by examiner

*Primary Examiner*—Nikita Wells
*Assistant Examiner*—Johnnie L Smith
(74) *Attorney, Agent, or Firm*—John W. LaBatt; Hoffman Warnick LLC

(57) ABSTRACT

A solution for sterilizing one or more hollow components of a device, such as a medical device, is provided. Ultraviolet radiation having one or more predominant wavelength(s) and a sufficient dose is generated and directed to an interior side of the hollow component(s). The predominant wavelength(s) is/are selected to harm one or more target organisms that may be present on the interior side. The ultraviolet radiation can be delivered by a structure that is periodically inserted and retracted into the hollow component. The structure can be configured to provide additional cleaning capability, such as suction, for removing matter that may be present in the hollow component.

21 Claims, 6 Drawing Sheets

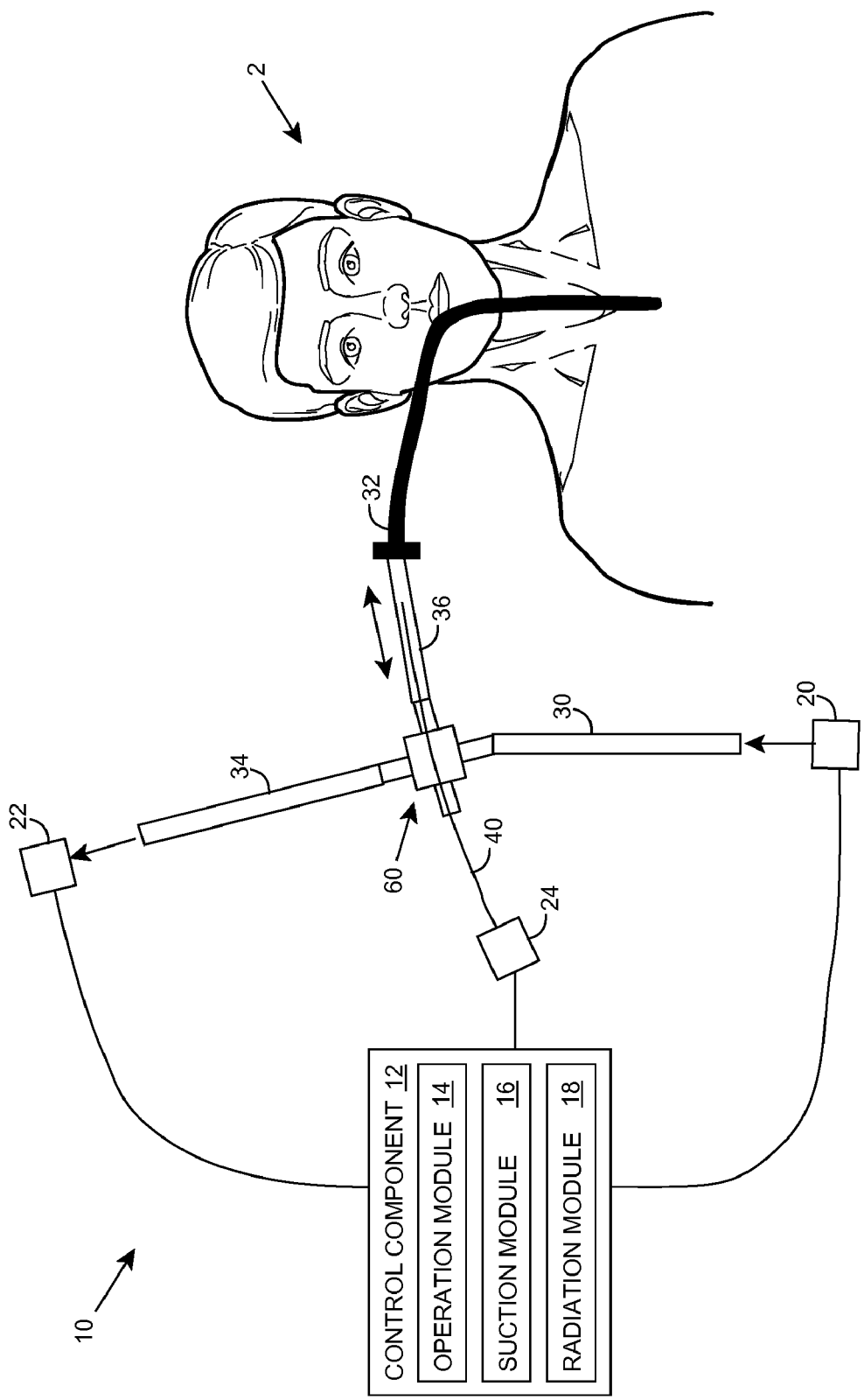

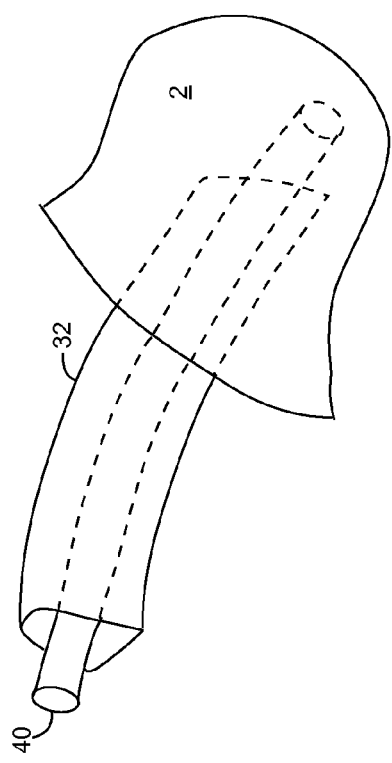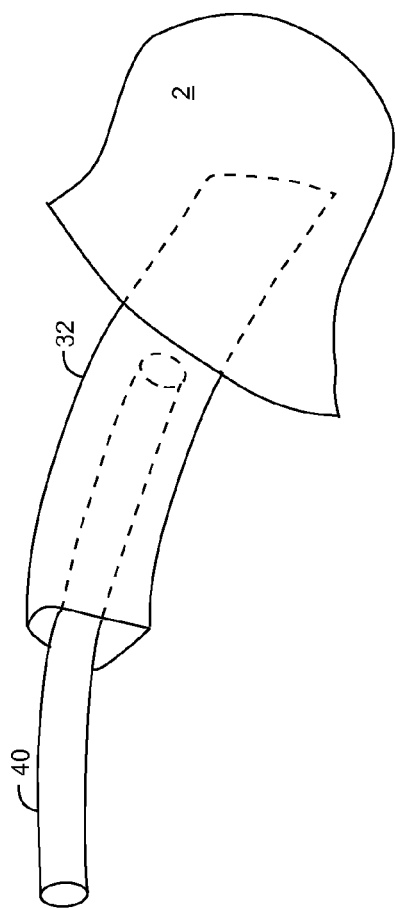

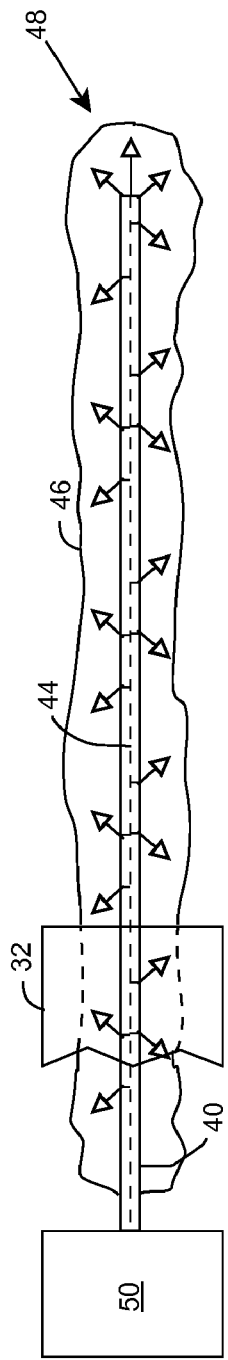
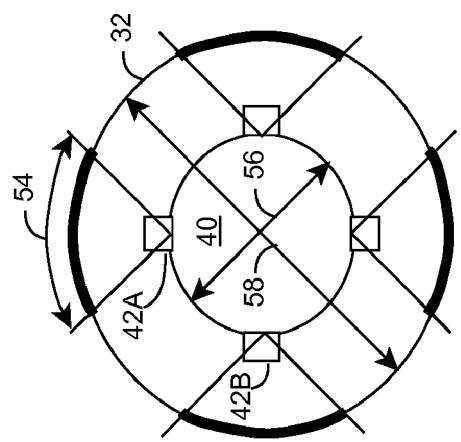

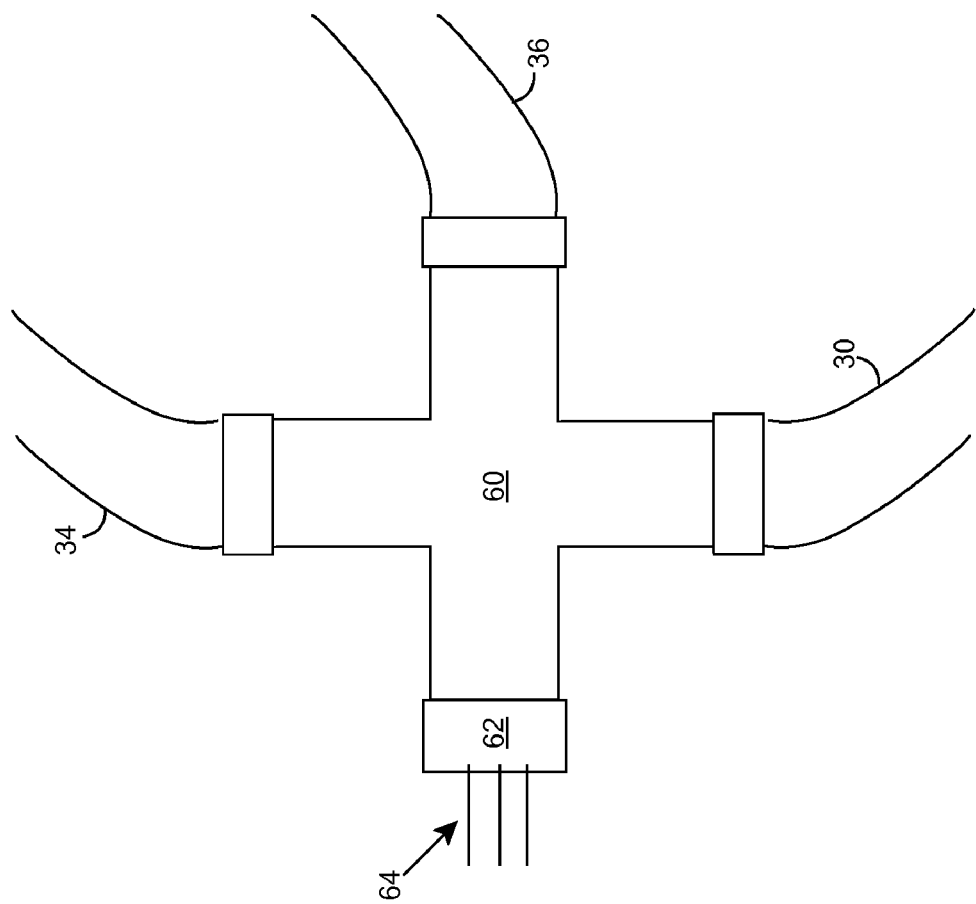

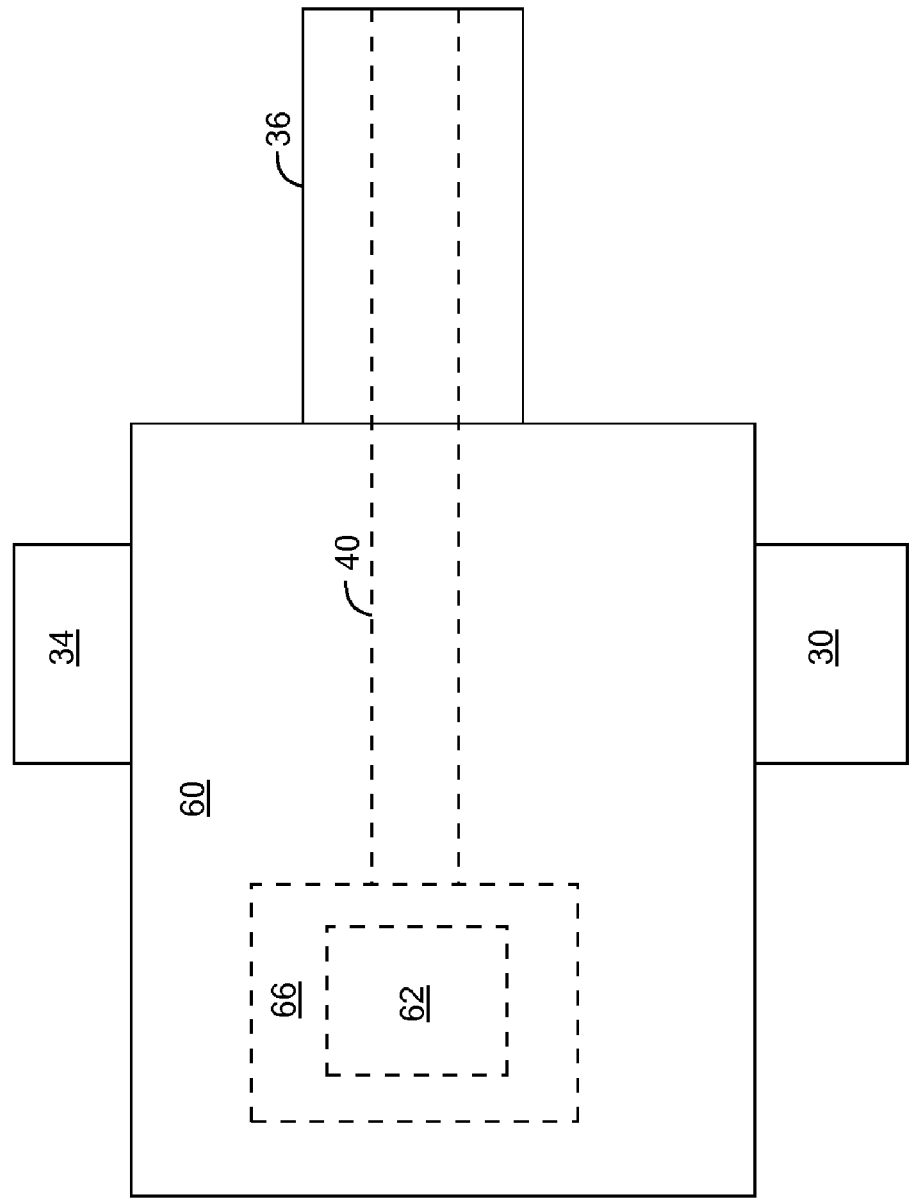

ULTRAVIOLET RADIATION STERILIZATION

CROSS-REFERENCE TO RELATED APPLICATIONS

The current application claims the benefit of U.S. Provisional Application No. 60/773,131, filed on 14 Feb. 2006, which is hereby incorporated by reference. The current application is related in some aspects to co-pending U.S. Utility application Ser. No. 11/380,512, filed on 27 Apr. 2006, which is hereby incorporated by reference.

FIELD OF THE INVENTION

Aspects of the invention relate generally to sterilization, and more particularly, to a solution for sterilizing a medical device using ultraviolet radiation.

BACKGROUND OF THE INVENTION

Ultraviolet radiation has been successfully used in purification and sterilization systems for various media, such as air, water, and food. Such a system includes a source of ultraviolet radiation that emits ultraviolet radiation having wavelength(s) close to the absorption peaks of biologically significant molecules of deoxyribonucleic acid (DNA) and proteins. The system sterilizes the media by exposing it to ultraviolet radiation of a sufficient power and for a sufficient exposure time to destroy the internal biomolecular structure of bacteria, viruses, protozoa, and other organisms, which may be present in the media.

Typically, the source of the ultraviolet radiation in an ultraviolet purification or sterilization system is a mercury lamp. To this extent, a low-pressure or a medium-pressure mercury lamp provides a linear spectrum of radiation with one or more peak lines having a wavelength that is in the relative vicinity to the DNA absorption line. For example, a low-pressure mercury lamp having a main peak at 253.4 nanometers (nm) is generally used in low-consumption residential water purification systems and residential air purification systems. Further, a medium-pressure mercury lamp having a higher radiation power and a multi-peak radiation spectrum is used in municipal systems with medium and high water consumption.

However, the use of a mercury lamp as the source of ultraviolet radiation has significant drawbacks. For example, mercury is an extremely dangerous element, thereby limiting the applications of mercury-based water and/or air purification systems. In particular, such a mercury-based water purification system is generally not used in transportation or individual applications. Further, a typical lifetime of the mercury lamp generally does not exceed ten thousand hours. Still further, the radiation spectrum of the ultraviolet radiation generated by the mercury lamp includes peak lines having characteristic wavelengths that do not exactly coincide with the absorption peaks of DNA and proteins and these peak lines cannot be controlled or adjusted, which results in a decrease in the efficiency of the system. Still further, mercury lamps are fragile and often bulky, which generally adds to the overall cost and/or size of the system and does not allow for a flexible design. Various other limitations are present as will be recognized by one of ordinary skill in the art.

BRIEF SUMMARY OF THE INVENTION

Aspects of the invention provide a solution for sterilizing one or more hollow components of a device, such as a medical device. Ultraviolet radiation having one or more predominant wavelength(s) and a sufficient dose is generated and directed to an interior side of the hollow component(s). The predominant wavelength(s) is/are selected to harm one or more target organisms that may be present on the interior side. The ultraviolet radiation can be delivered by a structure that is periodically inserted and retracted into the hollow component. The structure can be configured to provide additional cleaning capability, such as suction, for removing matter that may be present in the hollow component. The sterilization can be performed in a non-obstructive manner, which enables use of the component, and therefore the device, to continue during and after the sterilization.

A first aspect of the invention provides a medical sterilization system, the system comprising: means for generating ultraviolet radiation; and means for directing the ultraviolet radiation onto an interior side of a hollow component of a medical device.

A second aspect of the invention provides a method of sterilizing a medical device, the method comprising: generating ultraviolet radiation using a set of ultraviolet radiation sources; and directing the ultraviolet radiation onto an interior side of a hollow component of the medical device.

A third aspect of the invention provides a method of sterilizing a hollow elongated structure, the method comprising: generating ultraviolet radiation using a set of ultraviolet radiation sources; and inserting a second elongated structure into the hollow elongated structure, the second elongated structure directing the ultraviolet radiation onto an interior side of the hollow elongated structure.

A fourth aspect of the invention provides a system for sterilizing a hollow elongated structure, the system comprising: means for generating ultraviolet radiation; a second elongated structure; and means for inserting the second elongated structure into the hollow elongated structure, the second elongated structure directing the ultraviolet radiation onto an interior side of the hollow elongated structure.

A fifth aspect of the invention provides a computer program product stored on at least one computer readable medium, which when executed causes a computer system to implement a method of sterilizing a hollow structure, the method comprising: generating ultraviolet radiation using a set of ultraviolet radiation sources; and inserting a second structure into the hollow structure, the second structure directing the ultraviolet radiation onto an interior side of the hollow structure.

The illustrative aspects of the present invention are designed to solve one or more of the problems herein described and/or one or more other problems not discussed.

BRIEF DESCRIPTION OF THE SEVERAL VIEWS OF THE DRAWINGS

These and other features of the invention will be more readily understood from the following detailed description of the various aspects of the invention taken in conjunction with the accompanying drawings that depict various embodiments of the invention.

FIG. 1 shows an illustrative medical device according to an embodiment of the invention.

FIGS. 2A-B show illustrative positions of a sterilization structure according to an embodiment of the invention.

FIGS. 3A-C show illustrative configurations of a sterilization structure according to embodiments of the invention.

FIG. 4 shows an illustrative cross section of a sterilization structure within a tube according to an embodiment of the invention.

FIG. 5 shows an illustrative connector according to an embodiment of the invention.

FIG. 6 shows another illustrative connector according to an embodiment of the invention.

It is noted that the drawings are not to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 3A:
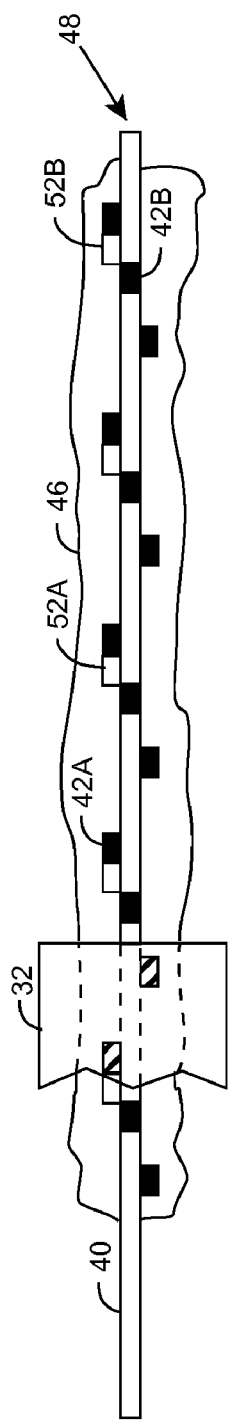

As indicated above, aspects of the invention provide a solution for sterilizing one or more hollow components of a device, such as a medical device. Ultraviolet radiation having one or more predominant wavelength(s) and a sufficient dose is generated and directed to an interior side of the hollow component(s). The predominant wavelength(s) is/are selected to harm one or more target organisms that may be present on the interior side. The ultraviolet radiation can be delivered by a structure that is periodically inserted and retracted into the hollow component. The structure can be configured to provide additional cleaning capability, such as suction, for removing matter that may be present in the hollow component. The sterilization can be performed in a non-obstructive manner, which enables use of the component, and therefore the device, to continue during and after the sterilization. As used herein, unless otherwise noted, the term "set" means one or more (i.e., at least one) and the phrase "any solution" means any now known or later developed solution.

Aspects of the invention generally relate to cleaning one or more surfaces of a device. In general, the device can comprise any type of device that includes hollow structure(s) within which any combination of air, gases, fluids, solids, and/or the like, may pass through, accumulate, or otherwise be present. In an illustrative embodiment, the device is a biological device, such as a medical device, and the surface(s) is/are on the interior of a hollow structure (e.g., tubing) that is included in the biological device, and which is used to provide the passage of air, fluids (e.g., biological, medical, and/or the like), solids, and/or the like.

Regardless, aspects of the invention provide a solution in which the surface(s) are sterilized using ultraviolet radiation. To this extent, the ultraviolet radiation can be directed at the surface(s) in such a manner as to harm (e.g., suppress growth, reduce an amount, kill, damage, injure, etc.) any organisms that may be present on the surface(s). The organism(s) can comprise any combination of various types of organisms, such as bacteria, viruses, protozoa, biofilms, mold, and/or the like. The discussion herein refers to the sterilization of one or more surfaces. As used herein, "sterilizing" and "sterilization" refer to harming one or more target organisms, and include purification, disinfection, and/or the like. Further, as used herein a "sterilized surface" includes a surface that is devoid of any live organisms, a surface that is devoid of any live targeted organisms (but which may include non-targeted organisms), and a surface that includes some live targeted organism(s), but which is substantially free of such organism (s).

Turning to the drawings, FIG. 1 shows an illustrative medical device 10 according to an embodiment of the invention. Medical device 10 includes a control component 12, which operates a delivery component 20, a removal component 22, and a cleaning component 24. In an embodiment of the invention, medical device 10 comprises any type of respiratory and/or breathing device, such as a mechanical ventilator, artificial respirator, or the like, which can assist and/or replace the spontaneous breathing of a patient 2. In this case, during operation of medical device 10, operation module 14 can operate delivery component 20 to periodically deliver air (e.g., oxygen, or an oxygen mixture) into patient 2 through a source tube 30 and an endotracheal tube 32. Similarly, operation module 14 can operate removal component 22 to periodically remove air (e.g., carbon dioxide) from patient 2 through endotracheal tube 32 and drainage tube 34. Delivery component 20 can deliver the air and removal component 22 can remove the air using any solution. However, it is understood that removal component 22 could comprise a passive system. Regardless, delivery component 20 and/or removal component 22 can include one or more sensors for obtaining data on the air (e.g., volume, content, etc.), which can be obtained by operation module 14. Operation module 14 can display the air data, maintain a history of the air data, make one or more adjustments to delivery component 20 and/or removal component 22 based on the air data, generate one or more alarms based on the air data, and/or the like.

In any event, during operation of medical device 10, matter, such as bodily fluids and/or the like, can accumulate in endotracheal tube 32 and/or connecting tube 36. As a result, connecting tube 36 and/or endotracheal tube 32 will require periodic cleaning and/or changing to maintain a clear airway for the air and/or prevent organism growth. To this extent, suction module 16 can periodically operate cleaning component 24 to insert/retract a sterilization structure 40 into/from endotracheal tube 32 and/or connecting tube 36.

FIGS. 2A-B show illustrative positions of sterilization structure 40 with respect to endotracheal tube 32 and patient 2 according to an embodiment of the invention. In FIG. 2A, sterilization structure 40 is shown inserted into endotracheal tube 32. As illustrated, both sterilization structure 40 and endotracheal tube 32 extend into patient 2. When inserted, sterilization structure 40 may extend beyond tube 32 to perform cleaning on a surface within patient 2. Alternatively, sterilization structure 40 can be inserted along substantially an entire length of endotracheal tube 32, without extending beyond endotracheal tube 32. In FIG. 2B, sterilization structure 40 is shown within endotracheal tube 32, but not within patient 2. Sterilization structure 40 can be moved along endotracheal tube 32 to clean an interior side of endotracheal tube 32 while it remains in patient 2 and functioning as part of medical device 10 (FIG. 1).

Returning to FIG. 1, sterilization structure 40 can comprise any type of elongated structure. The elongated structure can be substantially rigid or include sufficient flexibility to bend about a corner. In an embodiment of the invention, sterilization structure 40 comprises a tube, which can enable the removal of matter from an interior side of endotracheal tube 32 and/or connecting tube 36 using any solution. For example, suction module 16 can operate cleaning component 24 to remove matter from the interior side of endotracheal tube 32 and/or connecting tube 36 by sucking the matter through sterilization structure 40. In this case, it is understood that the amount of suction used by cleaning component 24 should be small enough so that the breathing of patient 2 is not interfered with in any significant manner. Cleaning component 24 can continuously or periodically suck matter through sterilization structure as sterilization structure 40 is inserted and/or removed from endotracheal tube 32 and/or connecting tube 36 using any solution. When an end of sterilization structure 40 is sufficiently close to an end of endotracheal tube 32, cleaning component 24 can reduce and/or stop the suction to prevent harming patient 2.

According to an embodiment of the invention, sterilization structure 40 directs ultraviolet radiation onto an interior side of endotracheal tube 32 and/or connecting tube 36. The ultraviolet radiation can comprise a set of predominant wavelengths. A predominant wavelength comprises a particular wavelength in the ultraviolet spectrum that is emitted by an ultraviolet radiation source at a higher power than other wavelengths within the ultraviolet spectrum. The predominant wavelength(s) can be selected to coincide with ultraviolet wavelength(s) that coincide with or are close to the absorption spectra of the targeted DNA and/or ribonucleic acid (RNA) containing organism(s). Upon absorption, the ultraviolet radiation will harm one or more organisms that may be present and/or grow on the interior side of tubes 32, 36 during use of medical device 10. To this extent, the ultraviolet radiation can include one or more predominant wavelengths that are within a range of approximately 200 nanometers to approximately 360 nanometers.

In an embodiment of the invention, the ultraviolet radiation includes one or more predominant wavelengths in a first ultraviolet wavelength region between approximately 250 nanometers and approximately 280 nanometers, which can destroy the DNA/RNA containing organism(s) that may be present. For an ideal air environment, the ultraviolet radiation can have a wavelength between approximately 262 nanometers and approximately 267 nanometers, however, it is understood that the appropriate wavelength(s) will be dependent on the particular mixture of media (e.g., air, water, blood, lymph, and/or the like) in the environment. Additionally, the ultraviolet radiation can include one or more predominant wavelengths in a second ultraviolet wavelength region between approximately 280 nanometers and approximately 360 nanometers, which can prevent the reproduction of DNA/RNA containing organism(s) that may be present. A direct sterilization effect may be possible in a range between approximately 280 nanometers and approximately 320 nanometers, however, other mechanisms and objects of sterilization may be effected by higher wavelengths of ultraviolet radiation. Additionally, the specific wavelength(s) utilized can be selected based on the target organism(s) using any solution.

In any event, radiation module 18 can operate cleaning component 24 to generate ultraviolet radiation using a set of ultraviolet radiation sources and/or direct the ultraviolet radiation using sterilization structure 40. As discussed herein, cleaning component 24 can periodically insert and retract sterilization structure 40 into/from endotracheal tube 32 and/or connecting tube 36. Radiation module 18 can operate cleaning component 24 to automatically generate the ultraviolet radiation while the sterilization structure 40 is being inserted, while the sterilization structure 40 is being retracted (e.g., after suctioning), and/or both. Regardless, sterilization structure 40 can deliver a sufficient dose of the ultraviolet radiation onto the interior side in order to harm any target organism(s), e.g., biofilm. In an embodiment of the invention, the set of ultraviolet radiation sources can generate sufficient ultraviolet radiation to enable sterilization structure 40 to deliver an ultraviolet dose in a range between approximately 3.5 $\mu J/cm^2$ to about 1000 $mJ/cm^2$.

The ultraviolet radiation source(s) can comprise any combination of various types of ultraviolet radiation sources, such as ultraviolet light emitting diodes (LEDs), ultraviolet laser diodes, mercury lamps (low- and/or medium-pressure), and/or the like. A particular combination of ultraviolet radiation source(s) can be selected based on the desired predominant wavelengths using any solution. Sterilization structure 40 can comprise any type of structure for directing ultraviolet radiation. For example, sterilization structure 40 can comprise a material that is at least substantially transparent with respect to ultraviolet radiation.

In an embodiment of the invention, cleaning component 24 controls a set of ultraviolet radiation sources that includes a plurality of ultraviolet diodes. Each ultraviolet diode can comprise any type of ultraviolet radiation emitting diode, such as a semiconductor LED, a compound semiconductor diode (e.g., AlInGaN/GaN), a nitride-based semiconductor ultraviolet LED, an ultraviolet laser diode, a periodic array of ultraviolet diodes, and/or the like. Collectively, the ultraviolet diodes can emit ultraviolet radiation having a substantially similar predominant wavelength or multiple predominant wavelengths.

Additionally, radiation module 18 can operate cleaning component 24 to adjust one or more properties of the ultraviolet radiation emitted by the ultraviolet diodes using any solution. For example, cleaning component 24 can adjust a predominant wavelength of the ultraviolet radiation emitted by an ultraviolet diode, an energy density of the ultraviolet radiation, and/or the like. To this extent, cleaning component 24 can provide any space and time distribution for controlling the ultraviolet diode(s). In an illustrative embodiment, cleaning component 24 can pulse one or more ultraviolet diodes emitting ultraviolet radiation having a particular predominant wavelength. When the ultraviolet radiation includes multiple predominant wavelengths, the ultraviolet radiation for each predominant wavelength can be generated continuously or pulsed. When two or more wavelengths are pulsed, the respective pulses can comprise different pulse durations and/or sequences.

Figure 3B:
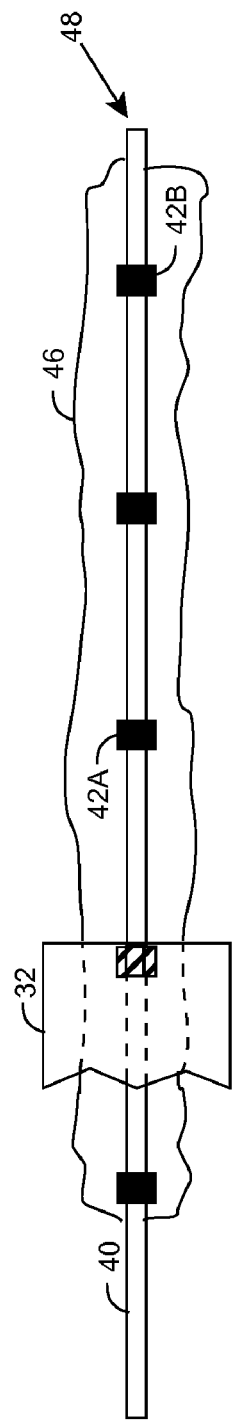

The plurality of ultraviolet diodes can be located on sterilization structure 40 using any solution. For example, FIGS. 3A-B show illustrative configurations of sterilization structure 40 including ultraviolet diodes thereon according to embodiments of the invention. Each sterilization structure 40 includes a plurality of ultraviolet diodes, such as ultraviolet diodes 42A-B, secured (e.g., attached, embedded, fixed, and/or the like) around its exterior and/or interior using any solution. Each ultraviolet diode 42A-B can be placed on sterilization structure 40 to emit ultraviolet radiation outward from and/or through sterilization structure 40 in a substantially perpendicular direction to the length of sterilization structure 40. As sterilization structure 40 is moved through, for example, endotracheal tube 32, the ultraviolet radiation will impinge on an interior side of endotracheal tube 32. Sterilization structure 40 can include wiring or the like, which enables cleaning component 24 (FIG. 1) to operate ultraviolet diodes 42A-B. The ultraviolet diodes 42A-B can be configured to enable independent operation of each ultraviolet diode 42A-B, independent operation of two or more subgroups of ultraviolet diodes 42A-B, operation of all ultraviolet diodes 42A-B as a single group, and/or the like.

Ultraviolet diodes 42A-B can be placed on sterilization structure 40 such that the ultraviolet radiation will impinge on substantially all locations of the interior side of, for example, endotracheal tube 32. Additionally, when multiple predominant wavelengths are desired for the ultraviolet radiation, the ultraviolet diodes 42A-B can be configured/operated such that substantially all locations of the interior side of endotracheal tube 32 are impinged by each of the predominant wavelengths. In FIG. 3A, ultraviolet diodes 42A-B are shown located on sterilization structure 40 in a spiral-type configuration, while in FIG. 3B, ultraviolet diodes 42A-B are shown located on sterilization structure 40 in multiple circular patterns. However, it is understood that these configurations are only illustrative and ultraviolet diodes 42A-B can be located on sterilization structure 40 using any solution.

Additionally, sterilization structure 40 can include a wave guiding structure for directing ultraviolet radiation outward from sterilization structure 40. For example, FIG. 3C shows an illustrative configuration of sterilization structure 40 including a wave guiding structure 44 according to an embodiment of the invention. Wave guiding structure 44 can comprise any type of material capable of delivering ultraviolet light emitted from an ultraviolet radiation source 50 to various points along sterilization structure 40. For example, wave guiding structure 44 can comprise a plurality of ultraviolet fibers, each of which terminates at an opening in sterilization structure 40, a diffuser, and/or the like. In any event, it is understood that sterilization structure 40 can include multiple locations on various sides from which ultraviolet radiation is emitted. These locations can be configured such that substantially all locations of the interior side of, for example, endotracheal tube 32, are impinged by the predominant wavelength(s). Additionally, it is understood that sterilization structure 40 can include wave guiding structure 44 in addition to ultraviolet diodes 42A-B (FIGS. 3A-B).

As shown in FIGS. 3A-C, a protective covering 46 can be included over at least a portion of sterilization structure 40. Protective covering 46 can prevent sterilization structure 40 from becoming contaminated due to contact with matter in, for example, endotracheal tube 32. Protective covering 46 can be made of any type of material, such as plastic or the like, which is transparent or substantially transparent with respect to ultraviolet radiation. As a result, ultraviolet radiation emitted from sterilization structure 40 can pass through protective covering and impinge, for example, endotracheal tube 32. As illustrated, protective covering 46 can loosely cover sterilization structure 40. Alternatively, protective covering 46 can comprise a rigid or semi-rigid covering. In either case, protective covering 46 can be permanently or temporarily attached to sterilization structure 40. In the latter case, protective covering 46 can be replaced after one or more uses. In FIGS. 3A-B, protective covering 46 is shown attached so that an interior end 48 of sterilization structure 40 remains exposed, which can enable sterilization structure 40 (e.g., a tube) to remove matter. Alternatively, in FIG. 3C, protective covering 46 is shown enclosing interior end 48 of sterilization structure 40, which can be used when sterilization structure 40 does not require an exposed portion.

Referring to FIGS. 1 and 3A, radiation module 18 and/or cleaning component 24 can receive feedback on the emitted ultraviolet radiation and adjust one or more properties of the generated ultraviolet radiation accordingly. For example, sterilization structure 40 can include a set of ultraviolet detectors, such as ultraviolet detectors 52A-B. Ultraviolet detectors 52A-B can comprise any type of ultraviolet sensing device, such as an ultraviolet-sensitive photodetector (e.g., an ultraviolet photodiode). Ultraviolet detectors 52A-B can be secured on sterilization structure 40 using any solution, and can be configured to sense ultraviolet radiation after it has reflected off of an interior surface of, for example, endotracheal tube 32. Sterilization structure 40 can include wiring or the like, which enables radiation module 18 and/or cleaning component 24 to receive feedback from the set of ultraviolet detectors 52A-B. Radiation module 18 and/or cleaning component 24 can use the feedback to ensure that ultraviolet diodes 42A-B deliver a sufficient dose for sterilization in, for example, an unstable current flow, changeable contamination, varying power supply conditions, and/or the like. Sterilization structure 40 and/or endotracheal tube 32 can include an exposed surface having a high reflection coefficient for the ultraviolet radiation, to help ensure a sufficient dose of ultraviolet radiation is delivered.

FIG. 4 shows an illustrative cross section of sterilization structure 40 within a tube, such as endotracheal tube 32, according to an embodiment of the invention. Sterilization structure 40 is shown including four ultraviolet diodes, such as ultraviolet diodes 42A-B, that are located around sterilization structure 40. Each ultraviolet diode 42A-B emits ultraviolet radiation, which impinges a portion of endotracheal tube 32. The impinged portion of endotracheal tube 32 varies based on an emission angle 54 of the ultraviolet radiation emitted from each ultraviolet diode 42A-B (and/or a wave guiding structure). In an embodiment, emission angle 54 can vary between approximately five degrees to approximately ninety degrees.

Additionally, the impinged portion will vary based on the relative diameters 56, 58 of sterilization structure 40 and endotracheal tube 32, respectively, and the location of sterilization structure 40 within endotracheal tube 32. In an embodiment, sterilization structure 40 has a diameter 56 that is approximately one half of the diameter 58 of endotracheal tube 32. For example, for an endotracheal tube 32 having a diameter 58 of approximately ten millimeters, sterilization structure 40 can comprise a diameter 56 of approximately five millimeters. In this manner, sterilization structure 40 can ensure that sufficient volume remains in endotracheal tube 32 to enable the continued functioning of medical device 10 (FIG. 1) even when sterilization structure 40 is present therein.

In any event, as illustrated, ultraviolet diodes 42A-B in a particular cross section may not emit ultraviolet radiation that impinges substantially all of endotracheal tube 32. To this extent, the locations of ultraviolet diodes 42A-B can be rotated to help ensure that substantially all of the interior side of endotracheal tube 32 will be impinged by ultraviolet radiation. Additionally, it is understood that more ultraviolet radiation sources (e.g., ultraviolet diodes 42A-B and/or wave guiding structures) can be included in a single cross-section to provide more comprehensive coverage of the interior side of endotracheal tube 32.

Returning to FIG. 1, medical device 10 includes other components that can be sterilized according to the invention. For example, tubes 30, 34 also may be sterilized using sterilization structure 40 in a manner similar to that described herein with respect to tubes 32, 36. Further, medical device 10 includes a connector 60 that connects tubes 30, 34, 36, and which can be configured to assist in directing the air flow through tubes 30, 34, 36 using any solution. Radiation module 18 and/or cleaning component 24 also can sterilize an interior side of connector 60.

To this extent, FIG. 5 shows an illustrative connector 60 according to an embodiment of the invention. Connector 60 includes connection points for tubes 30, 34, 36 to enable air flow through the respective tubes during operation of medical device 10 (FIG. 1). Additionally, connector 60 includes an ultraviolet radiation source 62 (e.g., one or more ultraviolet diodes), which can emit ultraviolet radiation onto an interior side of connector 60 to sterilize it. Connector 60 also includes an interface 64, which communicatively couples ultraviolet radiation source 62 with cleaning component 24 (FIG. 1), thereby enabling operation of ultraviolet radiation source 62 to perform the sterilization.

FIG. 6 shows another illustrative connector 60 according to an embodiment of the invention. As discussed herein, connector 60 includes connection points for tubes 30, 34, 36 to enable air flow there through. Further, connector 60 includes a sterilization component 66, which can control an ultraviolet radiation source 62 and a sterilization structure 40, and provide a communications link with cleaning component 24 (FIG. 1). In operation, cleaning component 24 can operate sterilization component 66 to periodically emit ultraviolet radiation using ultraviolet radiation source 62, insert/retract sterilization structure 40 into/from tube 36, and/or the like. Still further, cleaning component 24 can operate sterilization component 66 to remove matter from the interior of tube 36. In addition to sterilizing tube 36 and/or tube 32 (FIG. 1), sterilization structure 40 can be used to sterilize tubes 30, 34, and/or connector 60 in a similar manner. For example, sterilization component 66 can further control one or more mechanical structures in connector 60, which can direct sterilization structure into any tube 30, 34, 36 using any solution. Additionally, sterilization structure 40 can direct ultraviolet radiation onto an interior of connector 60 while it is retracted from tubes 30, 34, 36.

Returning to FIG. 1, a specific example is discussed. Suction module 16 and/or radiation module 18 can operate cleaning component 24 to periodically place (e.g., insert) sterilization structure 40 into and subsequently retract sterilization structure 40 from some or all of endotracheal tube 32 and/or connecting tube 36. Sterilization structure 40 can be inserted and subsequently retracted from substantially all of endotracheal tube 32, which has a total length of approximately thirty centimeters. Sterilization structure 40 can have a diameter of 5 millimeters, endotracheal tube 32 can have a diameter of 10 millimeters, and 0.2 millimeter×0.2 millimeter ultraviolet diodes can be mounted on a surface of sterilization structure 40. With Lambertian distribution, each ultraviolet diode will shine on an approximately 2.5 millimeter square area of the inner surface of endotracheal tube 32. As a result, a power density on the inner surface of endotracheal tube 32 will be approximately 150 times lower than at the surface of the ultraviolet diode. During a cleaning cycle (e.g, insertion and retraction), cleaning component 24 can move sterilization structure 40 at a speed of approximately three centimeters per second. The cleaning cycles can be repeated every fifteen minutes.

In this case, a typical duration for each cleaning cycle is approximately twenty seconds (ten seconds insertion+ten seconds retraction). With four cycles per hour, a total cleaning time would be approximately eighty seconds per hour. It is understood that a slower insertion/retraction speed and/or longer endotracheal tube 32 could be used, with which the duration of each cleaning cycle could increase to a range between approximately thirty seconds and approximately sixty seconds. Regardless, a required power to prevent the formation of biofilm is approximately 10 $\mu W/cm^2$. As a result, a total required dosage of ultraviolet radiation per hour can be calculated as: $10\ \mu W/cm^2 \times 3600\ seconds = 3.6\ mJ/cm^2$. For an exposure time of sixty seconds per hour, the required power density would be 0.6 $mW/cm^2$.

When endotracheal tube 32 is only exposed to ultraviolet radiation in one direction of the insertion/retraction cycle, a total exposure time can be calculated as 2.5 mm/1 cm*0.3 seconds=0.075 seconds, for four cycles per hour, the hourly exposure time will be approximately 0.3 seconds. In order to accumulate a sufficient dose to prevent the formation of biofilm in 0.3 seconds, a total power delivered during the 0.3 seconds will need to be approximately 12 $mW/cm^2$. To obtain this power density on the inner surface of endotracheal tube 32, a power density on the surface of the ultraviolet diode will need to be 1.8 $W/cm^2$, which is approximately 0.8 mW power for the 0.2 mm square ultraviolet diode. To irradiate substantially all of the inner surface of endotracheal tube 32, approximately twelve ultraviolet diodes (each irradiating approximately a 2.5 mm square) will be required. In an illustrative implementation, medical device 10 can use a sterilization structure 40 having twenty ultraviolet diodes, each having 1 mW of power. The ultraviolet diodes can emit ultraviolet radiation for ten seconds per cycle, which yields forty seconds per hour, which in turn yields sixteen minutes per day. For an ultraviolet diode lifetime of approximately 500 hours, sterilization structure 40 would last for nearly 1,900 days of operation of medical device 10.

While aspects of the invention have been shown and described with reference to "tubes", it is understood that the teachings apply equally to any hollow component having any shape. Similarly, while aspects of the invention have been shown and described with reference to a breathing device, the teachings apply equally to any type of medical device for any type of application, including, but not limited to, a catheter, a dental treatment system (e.g., suction), a medical drainage system, a blood supply system, an oxygen supply system, an anesthesia system, an endoscope probe, an ear diagnostic system, a hearing aid, nasal diagnostic and/or treatment system, a vaginal diagnostic system, a urological diagnostic and/or treatment system, a colonoscopy system, and/or the like. Further, while aspects of the invention have been shown and described with reference to a human patient, the teachings apply equally to medical devices and applications for animals and/or animal experimentation. Still further, while aspects of the invention have been shown and described with reference to a medical device, it is understood that the teachings apply equally to non-medical devices and applications, including but not limited to, a hazardous material suit, a diving suit, a space suit, and/or the like.

In certain applications, in addition to and/or alternative to cleaning an interior surface of a hollow structure, sterilization structure 40 can perform ultraviolet-based cleaning on a surface within patient 2. In particular, sterilization structure 40 can be inserted beyond a tube within patient 2 (e.g., as shown in FIG. 2A) and radiate ultraviolet radiation that impacts a surface of patient 2. In this manner, one or more organisms that may be present on the surface can be harmed. For example, sterilization structure 40 can be utilized as part of a root canal examining/curing ultraviolet treatment, endoscopy, bladder treatment, colonoscopy with combined diagnostics and treatment, and/or the like.

As described herein, control component 12 can operate delivery component 20, removal component 22, and/or cleaning component 24. To this extent, it is understood that control component 12 includes one or more input/output (I/O) devices for communicating with the various components 20, 22, 24. Further, control component 12 can include I/O device (s) for communicating with a user and/or one or more additional systems not shown. Communications between the various systems can occur over any combination of one or more types of wired and/or wireless communications links, such as a public or private network. Regardless, control component 12 can comprise any computing article of manufacture capable of implementing the processes described herein. For example, control component 12 can comprise one or more general purpose computing articles of manufacture capable of executing computer program code installed thereon. In this case, the functionality described in conjunction with each module 14, 16, 18 can be enabled by computer program code.

It is understood that modules 14, 16, 18 and components 20, 22, 24 are only illustrative of numerous combinations, which can be used to implement the processes described herein. Additionally, it is understood that a general purpose computing device and program code is only representative of various possible equivalent computing devices that may perform the processes described herein. To this extent, in other embodiments, the functionality described herein can be implemented by one or more computing articles of manufacture that include any combination of general and/or specific purpose hardware and/or computer program code. In each embodiment, the program code and hardware can be created using standard programming and engineering techniques, respectively. In any event, when control component 12 includes computer program code, it is understood that control component 12 will include various hardware components, such as a memory and processor, to enable the execution thereof. Similarly, components 20, 22, 24 may include computer program code and the corresponding hardware components.

As used herein, it is understood that the term "program code" means any expression, in any language, code or notation, of a set of instructions intended to cause computer system having an information processing capability to perform a particular function either directly or after any combination of the following: (a) conversion to another language, code or notation; (b) reproduction in a different material form; and/or (c) decompression. To this extent, program code can be embodied as one or more types of program products, such as an application/software program, component software/a library of functions, an operating system, a basic I/O system/driver for a particular computing and/or I/O device, and the like. Further, program code can be embodied in one or more computer-readable media, which comprise one or more of any type of tangible medium of expression (e.g., physical embodiment) of the program code.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A medical sterilization system, the system comprising:
    means for generating ultraviolet radiation;
    means for directing the ultraviolet radiation onto an interior side of a hollow component of a medical device, the means for directing including:
        a hollow elongated structure including means for emitting ultraviolet radiation outward from the elongated structure; and
        means for placing the elongated structure within the hollow component; and
    means for removing matter from the interior side using the elongated structure.

2. The system of claim 1, wherein the means for generating includes an ultraviolet diode.

3. The system of claim 1, wherein the means for generating includes a mercury lamp.

4. The system of claim 1, the means for generating and the means for emitting including a plurality of ultraviolet diodes on the elongated structure.

5. The system of claim 1, the means for emitting including a wave guiding structure in the elongated structure for directing the ultraviolet radiation outward from the elongated structure.

6. The system of claim 1, wherein the means for directing further includes means for periodically repeating the placing.

7. The system of claim 1, the elongated structure further including means for sensing ultraviolet radiation reflected off of the interior side, the means for generating including means for adjusting at least one property of the ultraviolet radiation in response to the sensed ultraviolet radiation.

8. The system of claim 1, the means for generating including means for adjusting at least one property of the generated ultraviolet radiation.

9. The system of claim 8, the at least one property comprising at least one of: a predominant wavelength or an energy density.

10. The system of claim 1, further comprising means for directing the ultraviolet radiation onto a surface of a patient.

11. A method of sterilizing a medical device, the method comprising:
    generating ultraviolet radiation using a set of ultraviolet radiation sources;
    directing the ultraviolet radiation onto an interior side of a hollow component of the medical device, the directing including:
        placing a hollow elongated structure within the hollow component; and
        emitting ultraviolet radiation outward from the hollow elongated structure; and
    removing matter from the interior side using the elongated structure.

12. The method of claim 11, the directing further including periodically repeating the placing.

13. The method of claim 11, further comprising:
    sensing ultraviolet radiation reflected off of the interior side using at least one photodetector located on the elongated structure; and
    adjusting at least one property of the generated ultraviolet radiation in response to the sensed ultraviolet radiation.

14. The method of claim 11, the generating including adjusting at least one property of the ultraviolet radiation.

15. The method of claim 11, the directing and generating occurring while the hollow component is being used.

16. The method of claim 11, the ultraviolet radiation having at least one predominant wavelength in at least one of: a first wavelength region between approximately 250 nanometers and approximately 280 nanometers or a second wavelength region between approximately 280 nanometers and approximately 360 nanometers.

17. A method of sterilizing a hollow elongated structure, the method comprising:
    generating ultraviolet radiation using a set of ultraviolet radiation sources;
    inserting a second elongated structure into the hollow elongated structure, the second elongated structure emitting and directing the ultraviolet radiation onto an interior side of the hollow elongated structure and sensing ultraviolet radiation reflected off of the interior side; and
    adjusting at least one property of the generated ultraviolet radiation in response to the sensed ultraviolet radiation.

18. The method of claim 17, the set of ultraviolet radiation sources including a plurality of ultraviolet diodes located on the second elongated structure.

19. The method of claim 17, the second elongated structure including a wave guiding structure.

20. The method of claim 17, further comprising periodically repeating the generating and inserting.

21. The method of claim 17, wherein the second elongated structure is hollow, the method further comprising removing matter from the hollow elongated structure using the second elongated structure.

* * * * *